US010792208B2

(12) United States Patent
Saunders et al.

(10) Patent No.: US 10,792,208 B2
(45) Date of Patent: Oct. 6, 2020

(54) CUSHIONING DEVICES WITH INTERNAL SHEAR ABSORBING LAYER

(71) Applicant: 5 Minds Mobility Inc., Oshawa (CA)

(72) Inventors: Kevin Saunders, Oshawa (CA); Jenifer Atkinson, Oshawa (CA)

(73) Assignee: 5 Minds Mobility Inc., Oshawa, ON (CA)

( * ) Notice: Subject to any disclaimer, the term of this patent is extended or adjusted under 35 U.S.C. 154(b) by 357 days.

(21) Appl. No.: 14/361,669

(22) PCT Filed: Dec. 3, 2012

(86) PCT No.: PCT/CA2012/050869
§ 371 (c)(1),
(2) Date: May 29, 2014

(87) PCT Pub. No.: WO2013/078566
PCT Pub. Date: Jun. 6, 2013

(65) Prior Publication Data
US 2015/0122266 A1 May 7, 2015

Related U.S. Application Data

(60) Provisional application No. 61/565,573, filed on Dec. 1, 2011.

(51) Int. Cl.
*A61G 15/12* (2006.01)
*A61G 7/057* (2006.01)
(Continued)

(52) U.S. Cl.
CPC ............... *A61G 15/12* (2013.01); *A61F 5/30* (2013.01); *A61G 5/1043* (2013.01);
(Continued)

(58) Field of Classification Search
CPC .......... A61G 5/1043; A61G 2005/1045; A61G 7/057; A61G 7/05707; A61G 7/05715;
(Continued)

(56) References Cited

U.S. PATENT DOCUMENTS 3,864,778 A * 2/1975 Vopat ...................... B43L 21/00
15/105
4,300,316 A * 11/1981 Ficurilli ..................... E06B 3/44
49/445
(Continued)

FOREIGN PATENT DOCUMENTS

CA 2488147 A1 5/2006
CA 2605081 A1 11/2006
(Continued)

OTHER PUBLICATIONS

Search Report and Written Opinion received for International application No. PCT/CA2012/050869 dated Feb. 21, 2013, 8 pages.

*Primary Examiner* — Alireza Nia
*Assistant Examiner* — Michelle J Lee
(74) *Attorney, Agent, or Firm* — Fiala & Weaver P.L.L.C.

(57) ABSTRACT

Shear-reduction cushioning devices are provided for the prevention of shear related wounds. Cushioning devices include upper and lower cushioning layers that contact each other through at least one internal shear reduction layer provided between the cushioning layers and extending over a shear reduction region, such that dynamic relative translation of the two cushioning layers is permitted within the shear reduction region while absorbing friction and shear internally. The interface between the cushioning layers (where the shear reduction layer is provided) may be angled relative to an external surface of the cushioning device. The cushioning layers may be attached or attachable to one another beyond the shear reduction region, to limit an
(Continued)

amount of relative translation of the cushioning layers and to re-center or reset the cushioning layers after use.

17 Claims, 7 Drawing Sheets

(51) Int. Cl.
| | | |
|---|---|---|
| *A61G 5/10* | (2006.01) | |
| *B32B 3/26* | (2006.01) | |
| *B32B 7/02* | (2019.01) | |
| *B32B 5/32* | (2006.01) | |
| *B32B 3/08* | (2006.01) | |
| *A61F 5/30* | (2006.01) | |

(52) U.S. Cl.
CPC ........ *A61G 5/1045* (2016.11); *A61G 7/05715* (2013.01); *B32B 3/085* (2013.01); *B32B 3/263* (2013.01); *B32B 5/32* (2013.01); *B32B 7/02* (2013.01); *A61G 2203/74* (2013.01); *B32B 2307/56* (2013.01); *B32B 2601/00* (2013.01)

(58) Field of Classification Search
CPC .. A61G 7/05723; A61G 15/12; A61G 15/125; A61G 5/1045; B32B 5/32; B32B 3/085; B32B 3/263; B32B 7/00–7/022; A47C 27/00; A47C 27/14; A47C 27/142; A47C 27/148; A47C 27/15; A47C 27/16; A47C 27/144; A47C 7/00–022; A47C 7/02–0213; A47C 7/029; A47C 7/14; A47C 7/18; A61F 5/30–32
See application file for complete search history.

(56) References Cited

U.S. PATENT DOCUMENTS

| | | | | |
|---|---|---|---|---|
| 4,470,366 | A * | 9/1984 | Williams | B63B 1/248 114/280 |
| 4,673,452 | A * | 6/1987 | Awdhan | A47C 27/144 156/254 |
| 5,333,921 | A | 8/1994 | Dinsmoor, III | |
| 5,511,260 | A * | 4/1996 | Dinsmoor, III | A47C 27/144 5/676 |
| 6,177,171 | B1 * | 1/2001 | Constantinides | A43B 7/1455 428/101 |
| 6,523,202 | B2 * | 2/2003 | Loomos | A47C 7/029 5/653 |
| 6,687,933 | B2 | 2/2004 | Habboub et al. | |
| 6,996,864 | B2 * | 2/2006 | Call | A61G 5/1043 297/452.27 |
| 7,555,796 | B2 * | 7/2009 | Lewis | A47C 20/04 5/690 |
| 8,919,347 | B2 * | 12/2014 | Carlson | A61G 7/057 128/889 |
| 2002/0178621 | A1 * | 12/2002 | Darby | A47C 7/029 5/653 |
| 2009/0144911 | A1 | 6/2009 | Lewis et al. | |
| 2013/0081208 | A1 * | 4/2013 | Dyevich | A61G 7/05715 5/727 |

FOREIGN PATENT DOCUMENTS

| | | |
|---|---|---|
| GB | 2405582 A | 3/2005 |
| GB | 2405582 B | 9/2005 |

* cited by examiner

CUSHIONING DEVICES WITH INTERNAL SHEAR ABSORBING LAYER

CROSS-REFERENCE TO RELATED APPLICATION

This application is a National Phase application claiming the benefit of PCT/CA2012/050869 filed on Dec. 3, 2012, in English, which further claims priority to U.S. Provisional Application No. 61/565,573, titled "CUSHIONING DEVICES WITH INTERNAL SHEAR ABSORBING LAYER" and filed on Dec. 1, 2011, the entire contents of which are incorporated herein by reference.

BACKGROUND

The present disclosure relates to devices for the reduction of discomfort and/or injury associated with shear and friction. More particularly, the present disclosure relates devices for the prevention of pressure related wounds and/or discomfort associated with friction and shear.

Pressure related wounds, also known as bedsores, typically result from an individual or patient remaining in a given postural position for a prolonged time period. For example, pressure related wounds are common in the elderly, bedridden patients, and individuals with reduced mobility who require the use of a wheelchair. Such wounds often present as ulcers or lesions that can become infected, thus leading to increased morbidity.

Pressure related wounds often arise when a patient or user slides relative to a supporting surface. Sliding can occur for a number of reasons. For example, a power wheelchair user who is active in the community may easily shift from a supportive position by virtue of rough sidewalk terrain or simply going up a curb. Wheelchair users who foot propel not only slide, but are at high risk for developing wounds due to the leg movement that is necessary to move their wheelchair in space.

Many pressure related wounds, such as those obtained by a wheelchair user, or by a bedridden patient, may not be strictly pressure related in origin, and may instead or additionally be a shear and/or friction related problem. For example, in the Braden Scale, which is a well-known and clinically proven and effective tool used by health care providers to determine the risk of a client developing a skin ulcer, one of the 5 major factors addressed is an assessment of friction and shear.

In the case of wheelchair users, a user that is seated on a surface that properly addresses immersion is still at risk for developing wounds related to the movement associated with foot propulsion. Therapists and wheelchair providers have a myriad of ways to deal with clients who slide. For example, wheelchairs may be set up to prevent the user from sliding forward, however this comes with its own set of problems. A wheelchair that is put in a slight tilt or "dump" may keep the client from sliding forward, however the risk is that they will have more difficulty with independent propulsion with their feet, and a dump position also puts more pressure on the ischial tuberosities and coccyx, which may in turn cause pressure wounds to develop.

Additionally, a wheelchair user will generally have more difficulty with transfers from even a slight fixed tilt position. Therapists dealing with a wheelchair user who sits in posterior pelvic tilt, (or the "sacral sitter"), often have to prescribe a cushion that will optimize pressure reduction and reduce slide tendencies. Wheelchair depth is negatively affected, and the user is often in need of repositioning from a caregiver which can increase exposure to friction and shear forces.

Prevention and therapeutic devices available in the wheelchair industry typically focus on pressure reduction and relief. Despite this primary focus on pressure reduction, clinical findings have shown friction and shear to be major indicators and risk factors associated with the development of pressure related wounds. Traditional foam or air cushions, or a hybrid of the two, or cushions with additional gel or other product that is added to the top of the cushion, do not address the issue of shear and friction that is a common and high risk problem. Some devices that do address friction and shear do so from the top of the product. For example, covers or overlays, or alternatively air products that are promoted as products that address shear, still allow the patient to move on top of the surface to a certain degree. Such an approach to friction and shear reduction sacrifices positioning.

SUMMARY

Shear-reduction cushioning devices are provided for the prevention of pressure related wounds. Cushioning devices include upper and lower cushioning layers that contact each other through at least one internal shear reduction layer provided between the cushioning layers and extending over a shear reduction region, such that dynamic relative translation of the two cushioning layers is permitted within the shear reduction region while absorbing friction and shear internally. The interface between the cushioning layers (where the shear reduction layer is provided) may be angled relative to an external surface of the cushioning device. The cushioning layers may be attached or attachable to one another beyond the shear reduction region, to limit an amount of relative translation of the cushioning layers and to re-center or reset the cushioning layers after use.

Accordingly, in a first aspect, there is provided a first cushioning layer; a second cushioning layer; at least one shear reduction layer provided between said first cushioning layer and said second cushioning layer and extending over a shear reduction region; wherein said first cushioning layer and said second cushioning layer are capable of relative translation under application of pressure to said first cushioning layer within said shear reduction region; and wherein said first cushioning layer is attached to said second cushioning layer at one or more locations beyond said shear reduction region such that relative translation of said first cushioning layer and said second cushioning layer is limited.

In another aspect, there is provided a cushioning device for reducing shear, comprising: a first cushioning layer; a second cushioning layer; at least one shear reduction layer provided between said first cushioning layer and said second cushioning layer and extending over a shear reduction region; wherein said first cushioning layer and said second cushioning layer are capable of relative translation under application of pressure to said first cushioning layer within said shear reduction region; and wherein said first cushioning layer is attachable to said second cushioning layer at one or more locations beyond said shear reduction region such that relative translation of said first cushioning layer and said second cushioning layer is limited.

In another aspect, there is provided a cushioning device for reducing shear, comprising: a first cushioning layer; a second cushioning layer; and at least one shear reduction layer provided at an interface between the first cushioning layer and the second cushioning layer, wherein the first cushioning layer and the second cushioning layer are capable of relative translation under application of pressure to the first cushioning layer; and wherein the interface is angled relative to an external surface of the device.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
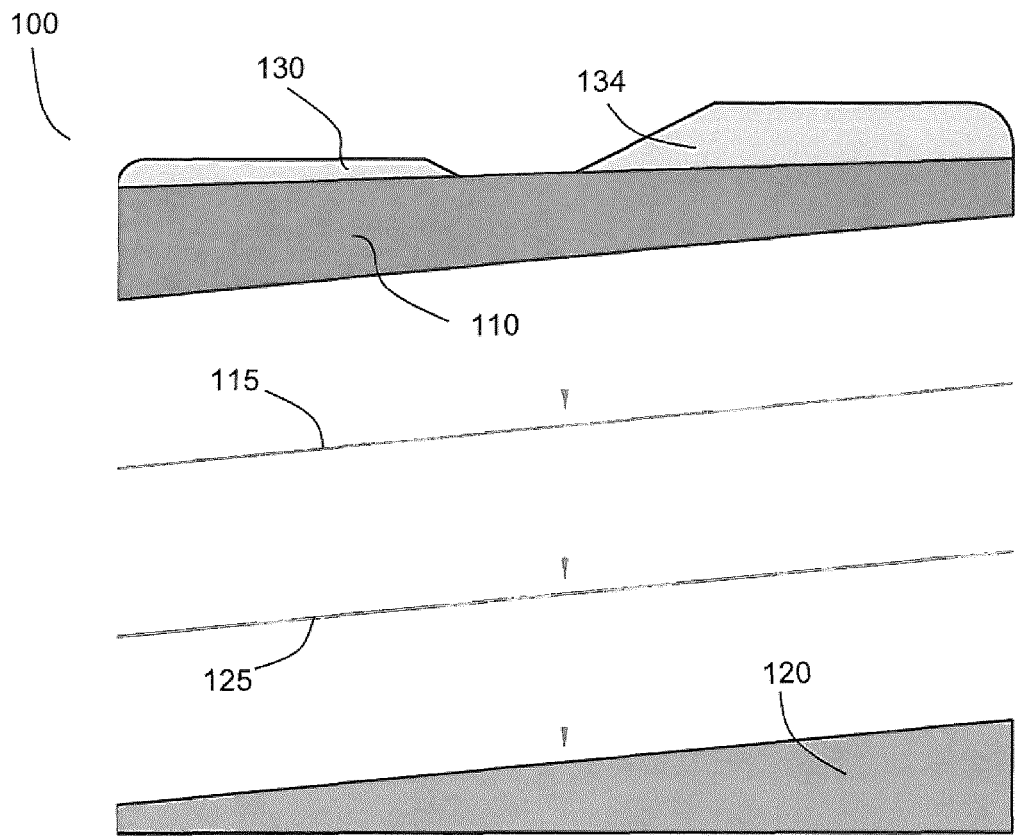
FIG. 1 shows an exploded side view of a shear reducing cushion including an internal shear reduction surface.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. It should be understood that the order of the steps of the methods disclosed herein is immaterial so long as the methods remain operable. Moreover, two or more steps may be conducted simultaneously or in a different order than recited herein unless otherwise specified.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

Embodiments of the present disclosure provide shear-reduction cushioning devices for the prevention of pressure related wounds. As described below, in selected embodiments, cushioning devices include upper and lower cushioning layers that contact each other through at least one internal shear reduction layer such that dynamic relative translation of the two cushioning surfaces is permitted. The inclusion of a shear reduction layer within the device supports relative translation of the two components, thus absorbing friction and shear internally. The internal shear reduction layer therefore allows a patient or user to sit, lay, or otherwise support themselves atop the surface and benefit from the cushioning layers (foam/gel/air etc) without shifting or sliding out of position in an undesirable way. Accordingly, solutions provided herein address shear and friction by allowing two component parts to move on each other without sacrificing position.

In some embodiments, the shear reduction layer is angled, over at least a portion of its extent, relative to an external surface of the cushioning device. The angled surface may be angled downwards toward a rear portion of the cushioning device for assisting with and providing compensation for the positioning of user seated on the cushioning device.

As will be shown below, the cushioning device may include one or more surface positioning features that assist in reducing or eliminating relative motion between the user and the upper layer of the cushioning device. Such surface features may include surface positioning contours and/or textured surface regions.

In some embodiments, the two cushioning layers are capable of relative translation over one region that includes the shear reduction layer, while the two cushioning surfaces are affixed to each other in at least one additional region for limiting or prohibiting the relative translation of the two cushioning surfaces. The shear reduction region is generally located such that when the weight of a user or patient is supported by the cushioning device, a substantial portion of the weight is received within the shear reduction region. By affixing the two cushioning layers at or over one or more additional regions, the two cushioning layers are prevented from global translation, misalignment, and potential separation of the layers. Furthermore, affixing the two layers at an additional location, the cushioning device inherently provides realignment, resetting, and/or re-centering of the two layers after use. In one embodiment, the cushioning layers are attached or attachable at a first location on one side of the shear reduction region, and at a second location on another side of the shear reduction region, such that relative translation of the cushioning regions is permissible between the first and second locations, but prohibited at, and optionally beyond, the first and second positions. In another embodiment, the cushioning layers are attached or attachable at a location on one side of the shear reduction region.

Figure 2:
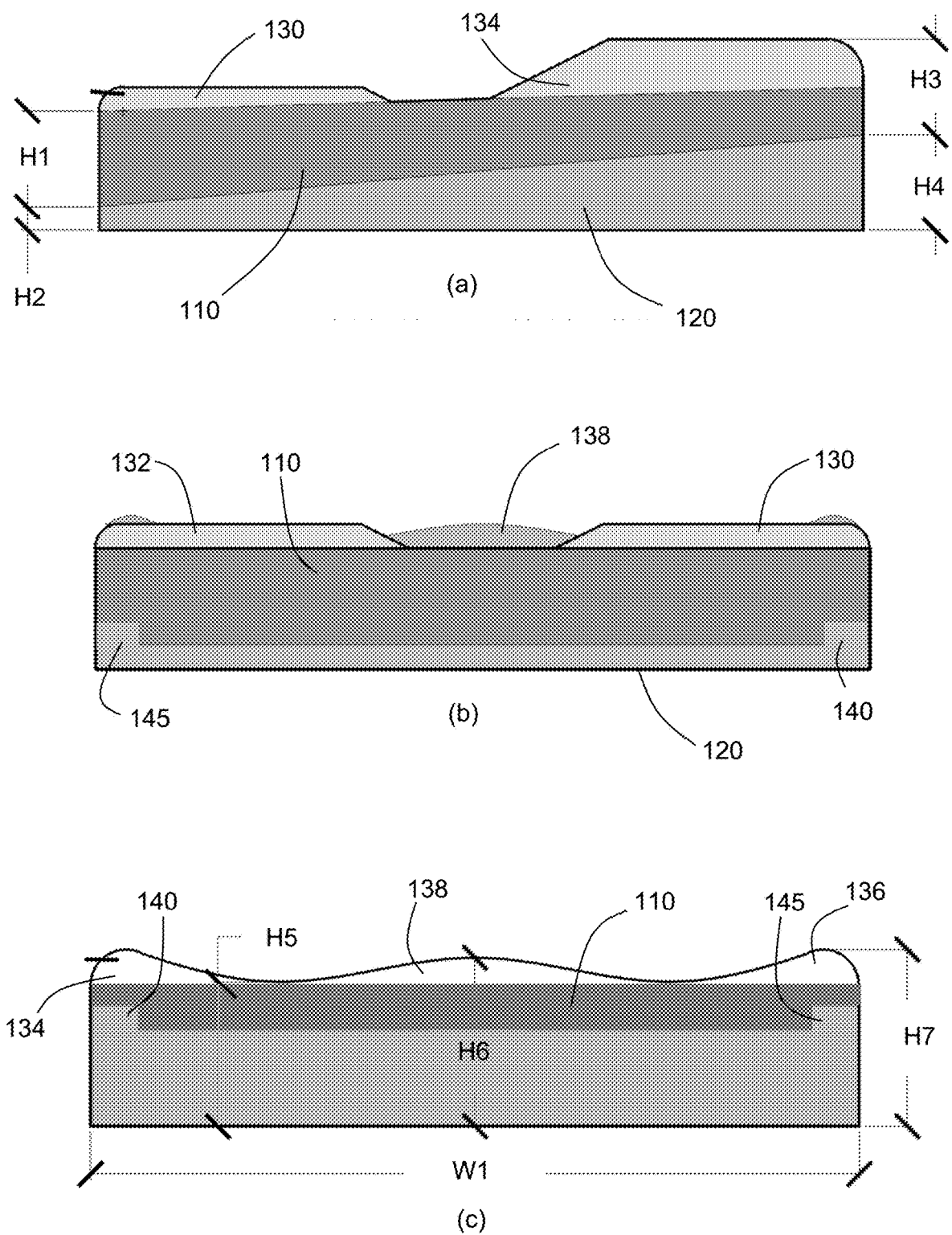
FIG. 2 shows different views of a shear reducing cushion, showing (a) a side view, (b) a front view, and (c) a rear view.
Figure 3:
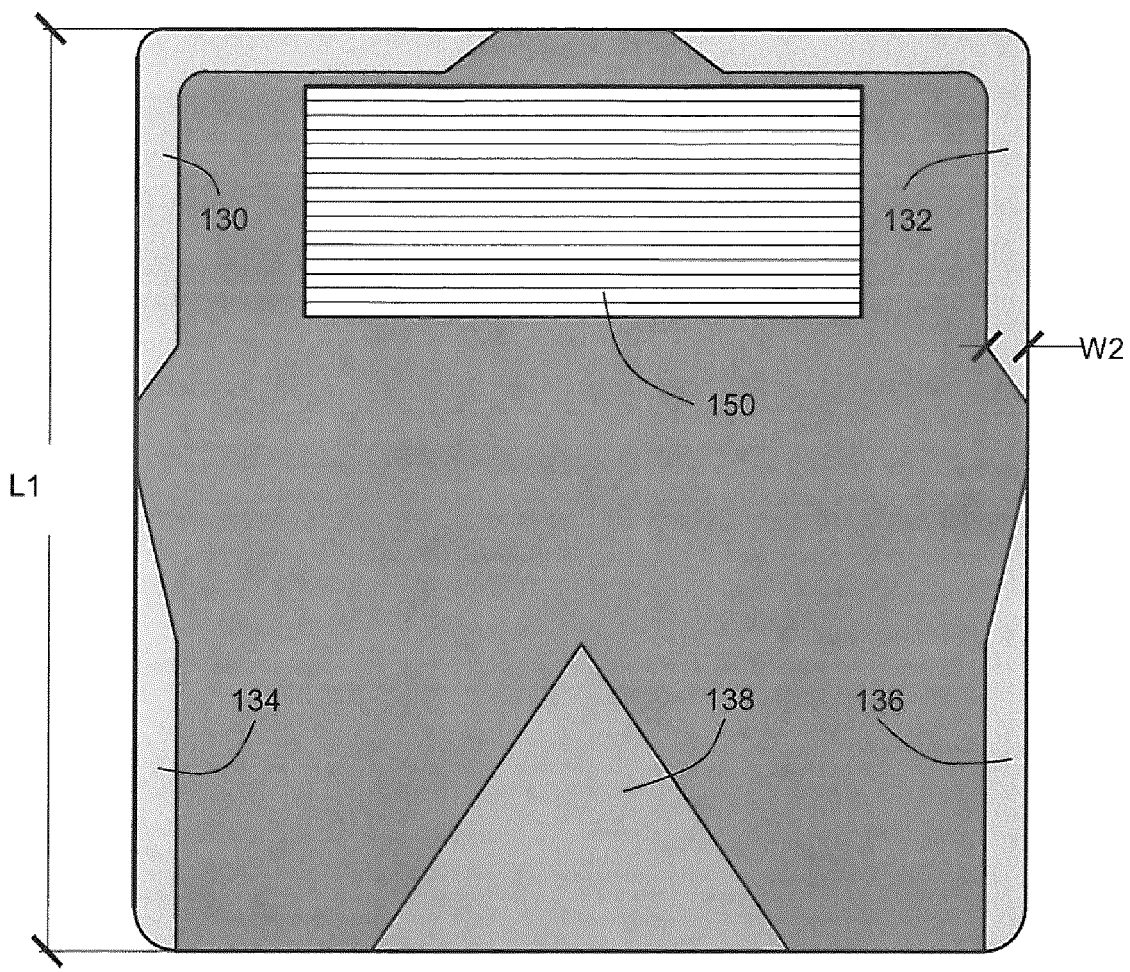
FIG. 3 shows a top view of a shear reducing cushion.

Referring now to FIGS. 1 to 3, an example embodiment of a cushioning device with an internal shear absorbing layer is provided. The cushioning device 100 includes upper cushioning layer 110, lower cushioning layer 120, and internal shear reduction layers 115 and 125. During construction of the cushioning device, shear reduction layer 115 is attached to upper cushioning layer 110, and shear reduction layer 125 is attached to lower cushioning layer 120. Accordingly, when brought into mutual contact to form the cushioning device, upper cushioning layer 110 contacts lower cushioning layer 120 through shear reduction layers 115 and 125, thus enabling relative translation of upper cushioning layer 110 and lower cushioning layer 120.

The addition of one or more shear reduction layers allows the user to sit on top of a base that supports them and provides necessary immersion to reduce the risk of pressure related sores, as well as creating movement on top of the lower cushioning layer that will absorb the friction and shear associated with movement. As described below, the use of a shear reduction layer within a cushioning device is applicable to a variety of positioning aids and sleep/sit surfaces.

Upper cushioning layer 110 and lower cushioning layer 120 may be made from any suitable compressible and cushioning materials, where the choice of a specific material or combination of materials may depend on the application and/or configuration of the device. Upper cushioning layer 110 and lower cushioning layer 120 may be made from the same or different materials. For example, in some applications, it may be beneficial for the upper cushioning layer 110 to be more compressible than the lower cushioning layer 120, or vice versa. In one non-limiting example, upper layer 110 may be formed from visco-elastic foam, and lower cushioning layer may be formed from high resiliency foam. In other example implementations, at least one layer of the upper and lower cushioning layers is made from a pressure reducing material. Examples of materials suitable for forming upper cushioning layer 110 and/or lower cushioning layer include molded or cut foam. In one example implementation, one or both of layers 110 and 120 may be formed from a foam having a density ranging from approximately 2.7-5.2 pounds per cubic foot.

In one embodiment, upper cushioning layer 110 may be a multi-component material that incorporates two or more cushioning materials. For example, upper conditioning layer 110 may include additional pressure relieving materials or components such as gel, air, and/or additional foam. Such additional cushioning materials may be provided, for example, at the back of cushion. The additional materials are provided such that the ability of upper cushioning layer 110 and lower cushioning layer 120 to slide and/or move in relation to each other is not impeded.

Shear reduction layers 115 and 125 may be made from any suitable material that allows for relative translation of upper cushioning layer 110 and lower cushioning layer 120 when pressure is applied to the cushioning device (for example, when supporting all or a portion of the weight of a user or patient). Suitable materials for the shear reduction layers include, but are not limited to, low friction materials such as nylon, Teflon™, gel, high viscosity liquid. It is to be understood that upper shear reduction layer 115 and lower shear reduction layer 125 need not be made from the same material. Shear reduction layers may be adhered to respective cushioning layers in any effective manner, including attaching a shear reduction layer to a respective cushioning layer, and applying a shear reduction coating to a respective cushioning layer.

In other embodiments, the upper and lower shear reduction layers 115 and 125 may be replaced by a single shear reduction layer. In one embodiment, the single shear reduction layer may be adhered to upper cushioning layer 110 or lower cushioning layer 120. In an alternative embodiment, the single shear reduction layer may be provided between upper cushioning layer 110 and lower cushioning layer 110, such that both upper cushioning layer 120 and lower cushioning layer 120 may translate relative the single shear reduction layer. Non-limiting examples of materials suitable for use as a single shear reduction layer include low shear fluid and gel.

FIGS. 2(*a*), 2(*b*) and 2(*c*) show lateral views of the example cushioning device 100, showing a side, rear and front view, respectively. FIG. 3 shows an overhead view of the example cushioning device 100. The shear reduction layers 115 and 125 reside between upper cushioning layer 110 and lower cushioning layer 120.

Also shown in FIGS. 2(*a*)-(*c*) and FIG. 3 are surface positioning features that include rear lateral positioning contours 130 and 132, front lateral positioning contours 134 and 136, and front central positioning contour 138. Such surface positioning features assist in reducing or eliminating relative motion between the user and the upper layer of the cushioning device, so that shear and friction are absorbed internally within the device at the shear reduction layer. Such surface positioning contours may be provided as additional portions that are affixed to upper cushioning layer 110, or may be formed directly within or on upper cushioning layer 110. FIG. 3 also includes an optional insertable surface 150 that provides an opportunity to introduce air, postural support surfaces, immersion options (via gel, alternative foam densities) between the user and upper cushioning layer 110 at areas prone to breakdown related to skeletal structures.

FIGS. 2(*a*)-(*c*) and FIG. 3 also show non-limiting example dimensions for a shear reduction seat cushion for use in a wheelchair. In one example implementation, the heights H1, H2, H3, H4, H5, H6 and H7 may be approximately 2", 0.5", 2", 2", 3", 3.5" and 4", respectively, and the corner radius may be approximately 0.5". The cushion width W1 may be approximately 1'6", the cushion length L1 may be approximately 1'6", and the width of lateral positioning contour 132 may be approximately 0.75".

In one example implementation, one or more external covers may be provided to enclose cushioning device 100. When enclosed, the cushioning layers are able to move freely on each other, where movement is controlled and/or limited by the secured cover. The cover may be made from a material with sufficient or suitable elasticity to enable limited relative translation of the two cushioning surfaces. The cover may be a protective cover, such as a cover that is weatherproofed and/or water resistant. An additional cover may be provided over the protective cover that is removable for laundering.

Referring to FIGS. 2(*b*) and 2(*c*), lower cushioning layer 120 may include lateral ridges 140 and 145 that mate corresponding features in upper cushioning layer 110. Lateral ridges 140 and 145 are beneficial in containing the position and motion of upper cushioning layer 110 and lower cushioning layer 120. As a result, upper cushioning layer 110 and lower cushioning layer are limited in direction of movement from the front of the cushion to the back of the cushion. This allows shear forces to be absorbed within the cushion, instead of being absorbed by the relative motion of user's body and upper cushioning layer 110. In one example implementation of the cushioning device shown in FIG. 2(*c*), the one or more shear absorbing layers 130 and 135 may extend over lateral ridges 140 and 145, thus extending the shear reduction layer over the full surface area of the cushion.

FIGS. 1-3 show an embodiment in which the interface between upper cushioning layer 110 and lower cushioning layer 120 where the one or more shear reduction layers are provided is angled relative to an external surface of the cushioning device. Accordingly, upper cushioning layer 110 and lower cushioning layer 120 are shaped as wedges that slide relative to each other under the application of pressure. In some embodiments, the interface may be angled such that a surface normal vector associated with the shear reduction layer is angled relative to the direction of gravity when the cushioning device is in use. In other embodiments, such as the example mattress embodiment disclosed below, the interface may be parallel to an external surface of the cushioning device.

The wedged shape of upper cushioning layer 110 and lower cushioning layer 120 can be beneficial in allowing for proper lower body positioning, particularly when cushioning device 100 is employed as a wheelchair cushion. For example, when fitting a wheelchair to a user, a significant amount of time may be spent adjusting the seat-to-floor height and the leg rest length, in order to provide comfortable and/or optimal body position. When in use, as the wheelchair user slides forward, the lower body distance changes as a result. By employing a cushioning device according to the embodiments shown in FIGS. 1-3, this increase in distance may be accommodated and/or compensated by the relative translation of upper cushioning layer 110 and lower cushioning layer 120. Furthermore, the angled interface (i.e. wedged shape) allows for easier repositioning of the user backwards in the wheelchair with the assist of gravity, where the repositioning utilizes the relative motion of upper cushioning layer 110 and lower cushioning layer 120 instead of the relative motion between the user and the cushioning. Additionally, the angled interface limits the amount of sacral sit of a user, thus helping to maintain the pelvis back in a neutral position.

In embodiments shown in FIGS. 1-3, the shear reduction surface extends from the front to the back of cushioning device 100 and is not interrupted. In another embodiment of a shear reduction cushioning device, the shear reduction surface is provided over only a portion of the device. For example, with reference to FIG. 2(c), the one or more shear absorbing layers may only extend over a limited portion of lateral ridges 140 and 145, such as only the vertical portion of the lateral ridges, or may not extend over the lateral edges at all. It has been found that by not providing the shear reduction layer over the lateral ridges, the amount of relative translation of upper cushioning layer 110 and lower cushioning layer 120 is further limited, and this limitation may be desirable in some applications and uses.

Figure 4:
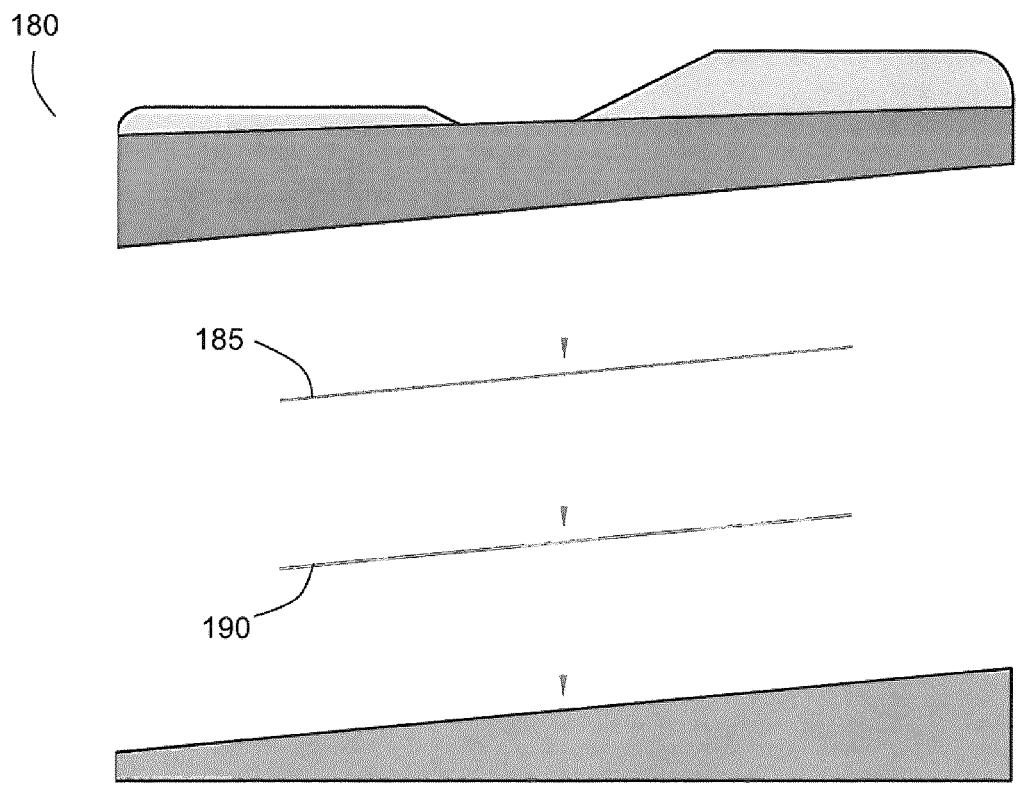
FIG. 4 shows an exploded side view of a chair cushion including an internal shear reduction surface that does not extend over the full area of the cushion.

FIG. 4 shows an alternative embodiment in which shear reduction layers 185 and 190 extend over only a portion of the cushioning device 180. In another example implementation, upper cushioning layer 110 and lower cushioning layer 120 may be a single structure that is slotted to allow the insertion of one or more shear reduction layers.

In one embodiment, beyond the extent of the shear reduction region, upper cushioning layer 110 and lower cushioning layer 120 may be attached or attachable (for example, bonded, glued, stitched, adhered through Velcro™, or otherwise joined). By attaching upper cushioning layer 110 and lower cushioning layer 120 at one or more positions or regions, a restoring force is provided to realign and limit the overall shift of the layers.

In other embodiments, upper cushioning layer 110 and lower cushioning layer 120 may be attached such that the shear reduction region is encapsulated or otherwise contained. Such an embodiment protects the integrity of the shear reduction layer, further limits the relative translation of the cushioning layers, and realigns, resets and/or re-centers the cushioning layers after use. For example, if the shear reduction layer is a single layer formed from a shear reduction fluid and/or gel, enclosure of the shear reduction layer prevents the shear reduction material from seeping out of the sides of the cushioning device when pressure is applied.

It is to be understood that the cushioning device shown in FIGS. 1-4 may be employed in wide variety of applications, including use as a wheelchair seat, seat cushion, and backrest. Additional applications and adaptations of this and other embodiments of the present disclosure are considered further below.

Figure 5:
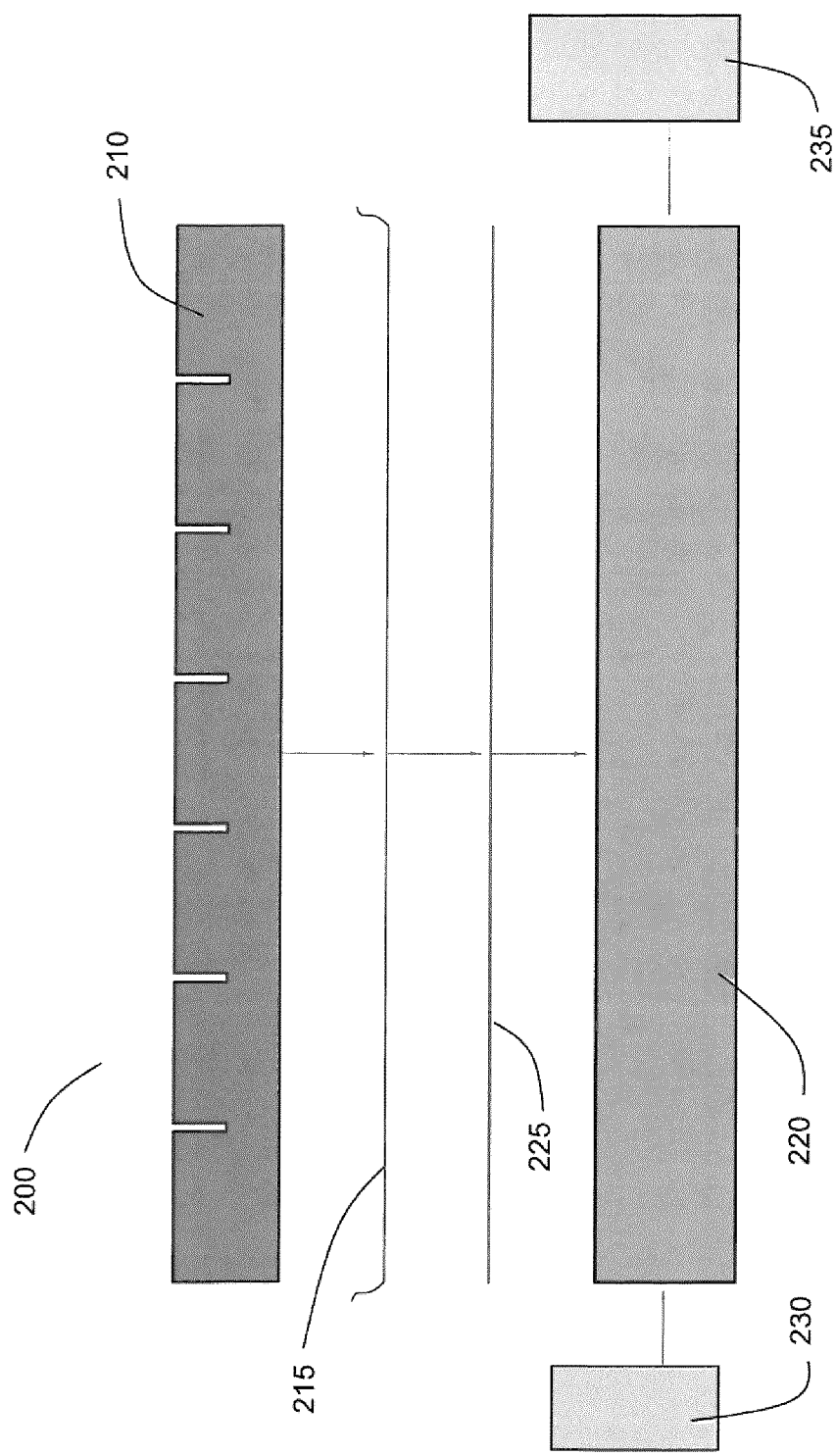
FIG. 5 shows a cross-sectional exploded view of mattress incorporating a shear reduction layer.
Figure 6:
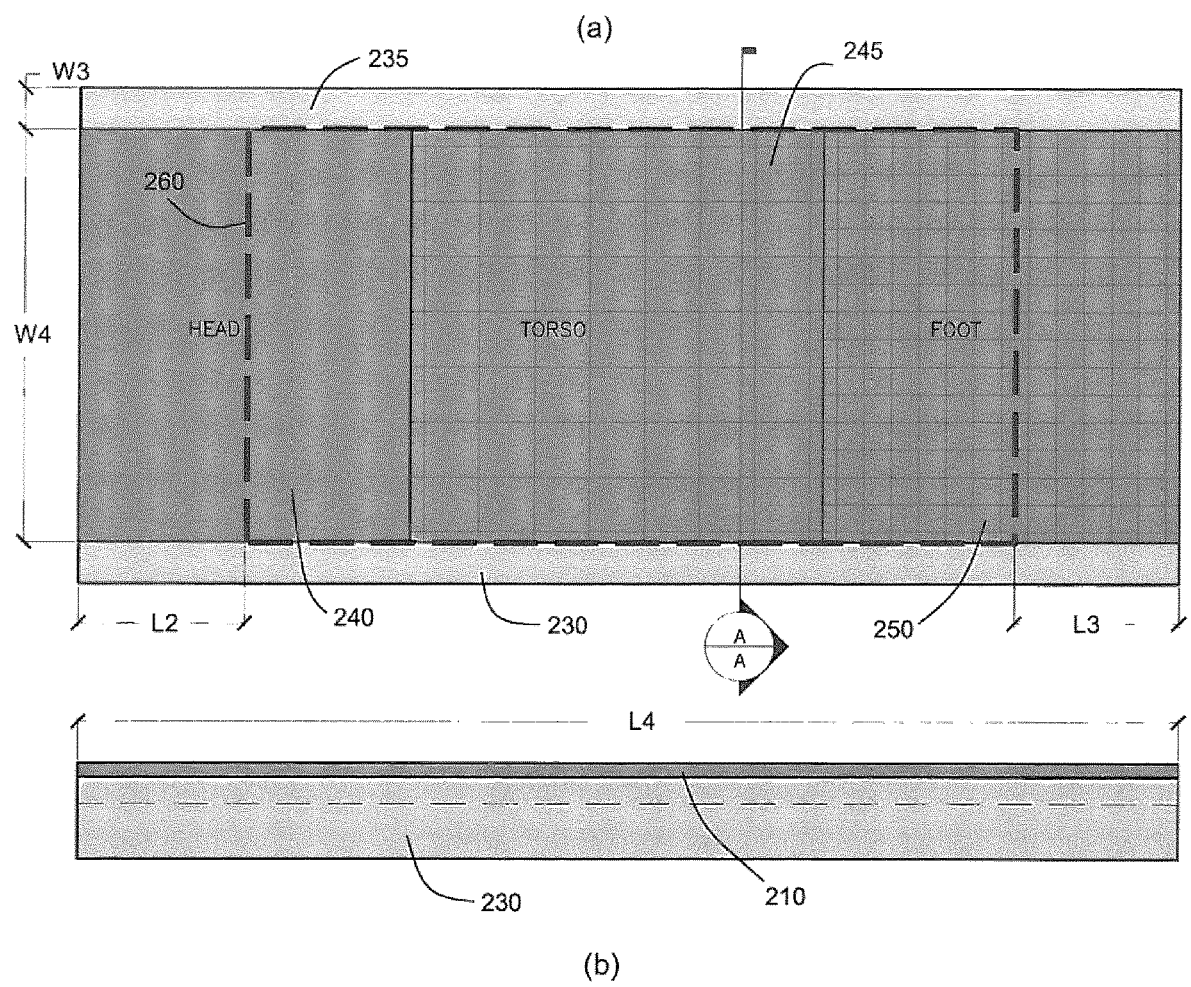
FIG. 6 shows different views of a mattress incorporating a shear reduction layer, showing (a) a top view and (b) a side view.
Figure 7:
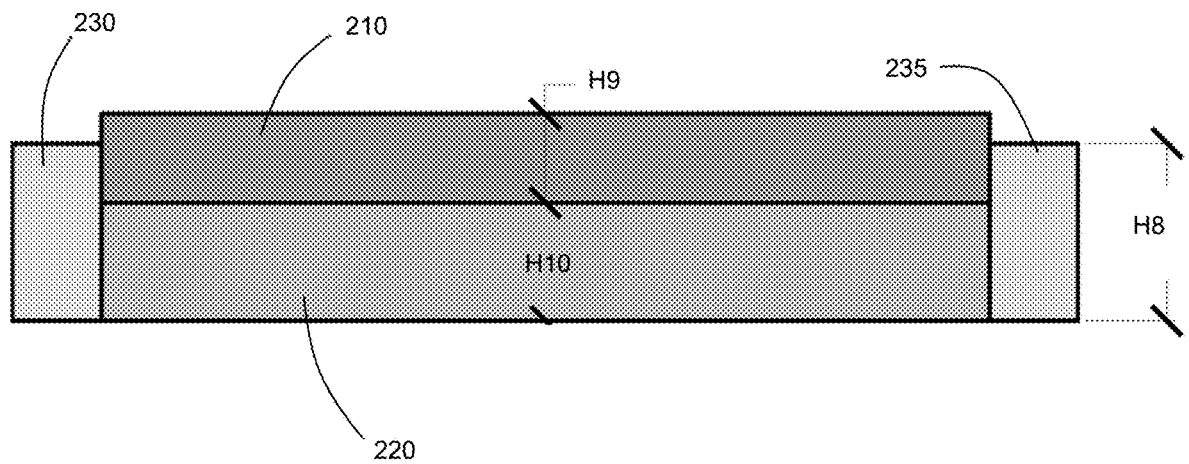
FIG. 7 shows a front view of a mattress incorporating a shear reduction layer.

FIGS. 5 to 7 show another example of a cushioning device according to the present disclosure, illustrating a shear-reduction mattress 200 incorporating one or more shear reduction layers. FIG. 5 shows a cross-sectional view of the shear reducing mattress, where upper cushioning layer 210 is shown contacting lower cushioning layer 220 through shear reduction layers 215 and 225. During construction of the mattress, shear reduction layer 215 is attached to upper cushioning layer 210, and shear reduction layer 225 is attached to lower cushioning layer 220. Accordingly, when brought into mutual contact to form the mattress, upper cushioning layer 210 contacts lower cushioning layer 220 through shear reduction layers 215 and 225, thus enabling relative translation of upper cushioning layer 210 and lower cushioning layer 220.

Upper cushioning layer 210 and lower cushioning layer 220 may be made from any suitable compressible and cushioning materials, where the choice of a specific material or combination of materials may depend on the application and/or configuration of the device, and upper cushioning layer 210 and lower cushioning layer 220 may be made from the same or different materials. Lower cushioning layer 220 may be formed from high-resiliency foam. Upper cushioning layer 210 may further include surface positioning features and/or textured surface features to assist in reducing or eliminating relative motion between the user and the upper layer of the mattress, so that shear and friction are absorbed internally within the mattress at the shear reduction layer. Mattress 200 may also include an optional insertable surface (similar to surface 150 in FIG. 3) that provides an opportunity to introduce air, postural support surfaces, immersion options (via gel, alternative foam densities) between the user and upper cushioning layer 210. Additionally, as described above, the mattress may be covered and/or enclosed by one or more external covers.

Furthermore, upper cushioning layer 210 may be a multi-component material that incorporates two or more cushioning materials. For example, upper conditioning layer 210 may include additional pressure relieving materials or components such as gel, air, and/or additional foam. Similarly, shear reduction layers 215 and 225 may be made from any suitable material that allows for relative translation of upper cushioning layer 210 and lower cushioning layer 220 when pressure is applied to the mattress (for example, when supporting all or a portion of the weight of a user or patient). Alternatively, the upper and lower shear reduction layers 215 and 225 may be replaced by a single shear reduction layer.

Referring again to FIG. 5, shear reducing mattress 200 may further include lateral cushioning segments 230 and 235 that are attached to lateral portions of lower cushioning layer 220 and maintain relative alignment of upper cushioning layer 210 and lower cushioning layer 220 during their relative translation. The central portion of the mattress (defined by upper cushioning layer 210 and lower cushioning layer 220 may have a height that is greater than that of lateral cushioning segments 230 to accommodate for the differences in density and indentation force deflection of the foams.

Optionally, as shown in FIG. 5, one or more of the shear reduction layers may be provided so that it contacts a surface of each lateral positioning segment, thereby reducing friction between the lateral cushioning members and upper cushioning layer 210 during translation.

FIG. 6 shows a top view of shear reducing mattress 200, which includes head 240, torso 245, and foot 250 areas. In the example embodiment shown, the one or more shear reduction layers are only provided over a portion of the total mattress area, and the shear reduction area 260 is shown by the dashed rectangle. Outside of the shear reducing area 260, upper cushioning layer 210 and lower cushioning layer 220 are adhered to each other (for example, bonded, glued, stitched, adhered through Velcro™, or otherwise joined). As discussed above with regard to the shear reduction cushioning device 100, by attaching upper cushioning layer 210 and lower cushioning layer 220 at one or more positions or regions, a restoring force is provided to realign and limit the overall shift of the cushioning layers.

Accordingly, in the present embodiment, the attachment of upper cushioning layer 210 and lower cushioning layer 220 causes the cushioning layers to realign automatically and limits the overall shift. Another advantage of the embodiment illustrated in FIG. 6 is that the presence of lateral cushioning segments 230 and 235 encapsulates the dynamic shear reduction portion of the mattress. Encapsulation allows for better control the amount of lateral shift, and is also beneficial for preserving the structural integrity and cleanliness of the shear reduction layer (thereby maintaining a constant coefficient of friction among layers). As noted above, encapsulation also prevents a flowable shear reduction material from seeping out of the sides of the cushioning device when pressure is applied.

FIGS. 6(a), 6(b) and 7 show non-limiting example dimensions for a shear reduction seat mattress. In one example implementation, the heights H8, H9, and H10 may be approximately 6", 3" and 4", respectively, the widths W2 and W3 may be approximately 3" and 2'6", and the total width W3 may be approximately 3'. The lengths L2 and L3 of the attachment regions without an internal shear reduction layer may be approximately 1' each, and the total mattress length may be approximately 6'8".

In the preceding disclosure, several example embodiments were provided in which one or more internal shear reduction layers are incorporated into a seat cushion and mattress. However, it is to be understood that the shear reduction embodiments disclosed below can be incorporated into or otherwise adapted for use with a wide range of products and device for the reduction of friction and shear. A non-limiting list of examples includes wheelchair cushions, mattresses, (including hospital bed mattresses), headrests, wheelchair backs and wheelchair trays.

Furthermore, it is to be understood that the scope of the present embodiments is not intended to be limited to clinical and/or therapeutic devices, or to users in vulnerable populations, and the present embodiments may be adapted for a wide range of consumer products, such as office chairs, home furniture, and seating in cars. In other examples, the present shear reduction embodiments may be adapted for use in infant, child and juvenile products such as mattresses, car seats, activity chairs, and infant swings.

The preceding embodiments may also be adapted to articles in which a potential for friction or shear exists, such as articles worn by a user, where the user may be, for example, a patient, athlete or worker. Such articles may not necessarily cause pressure related wounds due to friction and/or shear, but may cause discomfort, or minor chafing, abrasion, or other forms of irritation. Examples of such articles include wearable items such as backpacks, protective sporting equipment (such as hockey pads), footwear, footwear inserts, helmets, military equipment. Generally speaking, embodiments of the disclosure are applicable to any surface that offers the user protection/minimization from friction and/or shear forces.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A mattress for reducing shear, comprising:
   a first elongate cushioning layer;
   a second elongate cushioning layer located below said first elongate cushioning layer;
   a shear reduction layer provided between said first elongate cushioning layer and said second elongate cushioning layer, said shear reduction layer defining a shear reduction region configured to support a torso of a user, said shear reduction region extending over a portion of an area between said first elongate cushioning layer and said second elongate cushioning layer, wherein said shear reduction layer is adhered to one of said first elongate cushioning layer and said second elongate cushioning layer, and wherein said shear reduction layer is formed from a low-friction material, such that the other of said first elongate cushioning layer and said second elongate cushioning layer is translatable relative to said shear reduction layer when a shear force is generated under application of pressure to said first elongate cushioning layer within said shear reduction region, thereby internally absorbing the shear force; and
   wherein a lower surface of said first elongate cushioning layer is adhered to an upper surface of said second elongate cushioning layer over (i) a first spatially extended region extending from a first longitudinal end of said shear reduction layer to a first longitudinal end of the mattress and (ii) a second spatially extended region extending from a second longitudinal end of said shear reduction layer to a second longitudinal end of the mattress, said first spatially extended region and said second spatially extended region extending beyond said shear reduction layer such that relative translation of said first elongate cushioning layer and said second elongate cushioning layer is permissible within said shear reduction region but prohibited within the first spatially extended region and the second spatially extended region.

2. The mattress according to claim 1 wherein lateral surfaces of said second elongate cushioning layer are attached to lateral cushioning segments, and wherein said lateral cushioning segments extend beyond the upper surface of said second elongate cushioning layer for maintaining alignment of said first elongate cushioning layer and said second elongate cushioning layer.

3. The mattress according to claim 2 wherein said shear reduction layer contacts a surface of said lateral cushioning segments.

4. The mattress according to claim 1 wherein said shear reduction region is positioned to receive at least a portion of the user's weight.

5. The mattress according to claim 1 wherein an interface between said first elongate cushioning layer and said second elongate cushioning layer is angled relative to an external surface of said mattress.

6. The mattress according to claim 1 wherein said first elongate cushioning layer includes one or more surface features for reducing relative motion between the user and said first elongate cushioning layer.

7. The mattress according to claim 1 wherein said second elongate cushioning layer includes a lateral ridge configured to mate with a corresponding feature in said first elongate cushioning layer for guiding a relative motion of said first elongate cushioning layer and said second elongate cushioning layer.

8. The mattress according to claim 1 wherein said second elongate cushioning layer includes a high resiliency foam.

9. The mattress according to claim 1 wherein said first elongate cushioning layer includes a visco-elastic foam.

10. The mattress according to claim 1 wherein said first elongate cushioning layer includes a material selected from the group consisting of air, gel, foam, and a combination thereof.

11. The mattress according to claim 1 wherein said low-friction material comprises nylon or Teflon®.

12. A seat cushion for reducing shear when supporting a user in a seated configuration, the seat cushion comprising:
  a top wedge-shaped cushioning layer having a first upper surface, a first lower surface, and a thickness that increases from a front end of said top wedge-shaped cushioning layer to a rear end of said top wedge-shaped cushioning layer, such that said first lower surface is angled relative to said first upper surface;
  a bottom wedge-shaped cushioning layer having a second upper surface and a second lower surface and a thickness that decreases from a front end of said bottom wedge-shaped cushioning layer to a rear end of said bottom wedge-shaped cushioning layer, such that said second upper surface is angled relative to said second lower surface, wherein said top wedge-shaped cushioning layer is unfixed to said bottom wedge-shaped cushioning layer; and
  at least one shear reduction layer provided between said first lower surface and said second upper surface, thereby facilitating vertical repositioning of the user via relative translation of said top wedge-shaped cushioning layer and said bottom wedge-shaped cushioning layer when the user is seated on said top wedge-shaped cushioning layer without requiring relative motion between the user and said top wedge-shaped cushioning layer, wherein the entire at least one shear reduction layer is at an angle relative to the first upper surface of the top wedge-shaped cushioning layer.

13. The seat cushion according to claim 12 wherein lateral surfaces of said bottom wedge-shaped cushioning layer are attached to lateral cushioning segments, and wherein said lateral cushioning segments extend beyond said second upper surface of said bottom wedge-shaped cushioning layer for maintaining alignment of said top wedge-shaped cushioning layer and said bottom wedge-shaped cushioning layer.

14. The seat cushion according to claim 13 wherein at least one of said at least one shear reduction layers contacts a surface of said lateral cushioning segments.

15. The seat cushion according to claim 12 wherein said top wedge-shaped cushioning layer includes one or more surface features for reducing relative motion between the user and said top wedge-shaped cushioning layer.

16. The seat cushion according to claim 12 wherein said bottom wedge-shaped cushioning layer includes a lateral ridge configured to mate with a corresponding feature in said top wedge-shaped cushioning layer for guiding a relative motion of said top wedge-shaped cushioning layer and said bottom wedge-shaped cushioning layer.

17. A wheelchair comprising said seat cushion according to claim 12.

* * * * *